United States Patent
Cowan (10) Patent No.: US 9,014,803 B2
(45) Date of Patent: Apr. 21, 2015

(54) EFFICIENTLY DELIVERING ACOUSTIC STIMULATION ENERGY TO TISSUE

(71) Applicant: EBR Systems, Inc., Sunnyvale, CA (US)

(72) Inventor: Mark A. Cowan, Fremont, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 0 days.

(21) Appl. No.: 14/136,321

(22) Filed: Dec. 20, 2013

(65) Prior Publication Data

US 2014/0107725 A1    Apr. 17, 2014

Related U.S. Application Data (62) Division of application No. 11/460,850, filed on Jul. 28, 2006, now Pat. No. 8,634,908.

(60) Provisional application No. 60/704,620, filed on Aug. 1, 2005.

(51) Int. Cl.
| | | |
|---|---|---|
| A61N 1/37 | (2006.01) | |
| A61N 1/372 | (2006.01) | |
| A61N 1/378 | (2006.01) | |
| A61N 1/362 | (2006.01) | |

(52) U.S. Cl.
CPC .......... *A61N 1/37217* (2013.01); *A61N 1/3787* (2013.01); *A61N 1/362* (2013.01)

(58) Field of Classification Search
CPC .......... A61N 1/37217; A61N 1/3787
USPC ................................. 607/33, 60, 2
See application file for complete search history.

(56) References Cited

U.S. PATENT DOCUMENTS

| | | |
|---|---|---|
| 3,057,356 A | 10/1962 | Greatbach |
| 3,835,865 A | 9/1974 | Bowers |
| 4,343,312 A | 8/1982 | Cals et al. |
| 4,373,531 A | 2/1983 | Wittkampf et al. |
| 4,399,818 A | 8/1983 | Money |
| 4,498,478 A | 2/1985 | Bourgeois |
| 5,782,880 A | 7/1998 | Lantinen et al. |
| 5,843,136 A | 12/1998 | Zhu et al. |
| 6,428,484 B1 | 8/2002 | Battmer et al. |
| 6,584,358 B2 | 6/2003 | Carter et al. |
| 6,600,955 B1 | 7/2003 | Zierhofer |

(Continued)

FOREIGN PATENT DOCUMENTS

| | | |
|---|---|---|
| WO | WO 01/76687 A2 | 10/2001 |
| WO | WO 01/76687 A3 | 3/2002 |

OTHER PUBLICATIONS

European search report dated Feb. 16, 2009 for EP 06800623.8.

(Continued)

*Primary Examiner* — Eric D. Bertram
(74) *Attorney, Agent, or Firm* — Wilson Sonsini Goodrich & Rosati (57) ABSTRACT

A system for delivering an electrical stimulation pulse to tissue comprises a controller-transmitter and a receiver-stimulator. The controller-transmitter includes circuitry having an energy storage capacitor. The capacitance of the energy storage capacitor is adjusted to improve the efficiency of energy delivered from the receiver-stimulator to tissue by modifying the geometry of an acoustic drive burst from the controller-transmitter.

13 Claims, 7 Drawing Sheets

(56) References Cited

U.S. PATENT DOCUMENTS

| | | |
|---|---|---|
| 8,634,908 B2 | 1/2014 | Cowan |
| 2004/0172083 A1* | 9/2004 | Penner .......................... 607/35 |
| 2005/0065426 A1 | 3/2005 | Porat et al. |
| 2006/0136004 A1* | 6/2006 | Cowan et al. ................. 607/33 |
| 2006/0136005 A1 | 6/2006 | Brisken et al. |
| 2007/0027508 A1 | 2/2007 | Cowan |

OTHER PUBLICATIONS

International preliminary report on patentability dated Feb. 5, 2008 for PCT/US2006/029971.

International search report and written opinion dated Mar. 21, 2007 for PCT/US2006/029971.

Office action dated Jan. 6, 2010 for U.S. Appl. No. 11/460,850.

Office action dated Jun. 4, 2013 for U.S. Appl. No. 11/460,850.

Office action dated Jun. 23, 2010 for U.S. Appl. No. 11/460,850.

Soykan. Automated Piecewise Linear Modeling of Pacing Leads. Engineering in Medicine and Biology Society, Engineering Advances: New Opportunities for Biomedical Engineers. Proceedings of the 16th Annual International Conference of the IEEE (Nov. 3-6, 1994); vol. 1, pp. 53-54.

* cited by examiner

EFFICIENTLY DELIVERING ACOUSTIC STIMULATION ENERGY TO TISSUE

The present application is a divisional of U.S. patent application Ser. No. 11/460,850, now U.S. Pat. No. 8,634,908 filed Jul. 28, 2006, which claims the benefit of provisional U.S. Application No. 60/704,620, filed Aug. 1, 2005, the full disclosures of which are incorporated herein by reference.

BACKGROUND OF THE INVENTION

1. Field Of Invention

The systems and methods of this invention relate to pacing treatment of the heart by means of an implantable device, more specifically to systems and methods for providing such pacing without the use of conventional lead/electrode systems by transmitting pacing energy acoustically from an implanted or externally located transmitter to an implanted receiver-stimulator. Still more specifically, the present invention provides methods to improve the pacing pulse shape and efficiencies of such a pacemaker system.

In conventional pacemaker systems that apply an electrical pulse to the heart through a lead wire terminated at an electrode structure, considerable effort has been expended to optimize the shape of the electrical pacing pulse. This work has been driven primarily by two factors: 1) the constant need to optimize energy efficiency in the pacemaker to obtain maximum battery life, and/or minimize the size of the implanted device; and 2) the need in all modern conventional (wired) pacemakers to use the stimulating electrode to immediately sense, following stimulation, the electrogram signal from the cardiac tissue.

An early cardiac pacemaker patent (U.S. Pat. No. 3,057,356 by Greatbatch) shows, in one embodiment, the use of a storage capacitor between the output circuitry and the electrode attached to the heart, the capacitor providing the pulse generator with a lower output impedance and thus enabling a higher initial current to the electrode as compared to a directly-coupled output circuit. Most modern pacemaker designs still use a coupling/storage capacitor in the output circuit.

One undesirable effect of applying a pacing stimulus to cardiac tissue is electrode polarization, or generation of an after-potential, at the electrode-tissue interface. Depending on the amplitude of the stimulus, the after-potential can remain at hundreds of millivolts immediately after the stimulus, decaying to zero over the course of tens of milliseconds. In modern pacemakers, the stimulation electrode is also typically used to detect the electrogram of the heart; therefore, the presence of an after-potential may inhibit detection of an evoked response immediately after stimulation. The use of a capacitively-coupled output circuit alone reduces the after-potential by lowering the average DC component of the pacing waveform. However, in most cases, additional techniques are required to enable the measurement of evoked potentials following pacemaker stimulation. Methods to accomplish this have included applying a bi-phasic waveform (U.S. Pat. No. 3,835,865 by Bowers), or by applying more complex stimulation waveforms (U.S. Pat. No. 4,343,312 by Cals et al., and U.S. Pat. No. 4,373,531 by Wiitkampf et al.), or by discharging the polarization potential after the stimulus pulse (U.S. Pat. No. 4,399,818 by Money, U.S. Pat. No. 4,498,478 by Bourgeois, and U.S. Pat. No. 5,843,136 Zhu et al.). Other methods have been disclosed to further control and optimize the shape of the pacemaker stimulation waveform to produce a more energy efficient system (U.S. Pat. No. 5,782,880 by Lahtinen et al.).

As described in co-pending provisional application Ser. No. 11/315,523, and Ser. No. 11/315,524, a method of cardiac and other tissue stimulation uses one or more implantable acoustic receiver-stimulators for cardiac or other tissue stimulation, along with an implanted or externally-applied acoustic controller-transmitter. The implanted receiver-stimulator device comprises a piezoelectric sensor component, which passes an alternating current signal representing the acoustic field impinging upon it to a rectifier/filter circuit. The circuit functions to convert the AC signal from the piezoelectric sensor to a substantially DC waveform, the waveform being present for as long as the piezoelectric sensor is within an acoustic driving field, and importantly, the waveform produced essentially duplicates the shape of the envelope--contour of the peaks and valleys--of the transmitted acoustic energy. The rectifier/filter circuit might typically comprise a half wave rectifier, a full wave rectifier, or a voltage doubler circuit, to recite just a few possible implementations, followed by a filter comprising a series inductor or a parallel capacitor or combinations thereof, again to recite just a few possible implementations. Lastly, the tissue contacting electrodes might be typical of the current state-of-the-art in implantable electrode design and materials.

The transmitted acoustic energy is produced either by an acoustic controller-transmitter implanted beneath the skin of the subject and powered by a battery, or an externally positioned transducer controlled and powered by external means. For an implanted acoustic controller-transmitter, clinical utility requires that the device have a reasonable size (typical of current pacemakers) and that the device function without recharging for a period in excess of three years, preferably seven years. Such a temporal performance requirement places significant demands on the overall efficiency of the system. These demands are not unlike those faced by the first and all subsequent conventional pacemaker systems, which have been addressed by many improvements since the introduction of implantable pacemakers. The methods described herein directly attend to the demands of energy efficiency in a wireless pacemaker system utilizing acoustic energy and signal transmission, and also allow significant reduction in the physical size of such a device.

The issue of sensing an intrinsic or evoked electrogram through the same electrode used for stimulation is resolved by the co-pending applications mentioned above, which describe a system where the electrogram is sensed remotely from the stimulating electrode by means incorporated into the acoustic controller-transmitter device. More advanced versions of the receiver-stimulator could incorporate means to sense the electrogram and either process the information directly or transmit it back to the controller-transmitter through acoustic or other transmission methods. With such advancements, the process of sensing the electrogram would benefit from the stimulation waveform control produced by the methods describe in this disclosure.

2. Description of the Background Art

U.S. Pat. No. 3,057,356, W. Greatbatch, Medical Cardiac Pacemaker, October 1962; U.S. Pat. No. 3,835,865, D. L. Bowers, Body Organ Stimulator, September 1974; U.S. Pat. No. 4,343,312, G. Cals et al., Pacemaker Output Circuit, August 1982; U.S. Pat. No. 4,373,531, Wittkampf et al., Apparatus for Physiological Stimulation and Detection of Evoked Response, February 1983; U.S. Pat. No. 4,399,818, Money, Direct-Coupled Output Stage for Rapid-Signal Biological Stimulator, August 1983; U.S. Pat. No. 4,498,478, Bourgeois, Apparatus for Reducing Polarization Potentials in a Pacemaker, February 1985; U.S. Pat. No. 5,782,880, Lahtinen et al., Low Energy Pacing Pulse Waveform for Implantable Pacemaker, July 1998; U.S. Pat. No. 5,843,136, Zhu et al., Pacing Output Circuitry for Automatic Capture Threshold Detection in Cardiac Pacing Systems, December 1998; Saksena and Goldschlager: "Electrical Therapy for Cardiac Arrhythmias-Pacing, Antitachycardia Devices, Catheter Ablation", W.B. Saunders Co, Philadelphia, 1990; 0. Soykan: Automated Piecewise Linear Modeling of Pacing Leads, Medtronic Inc., Fridley, Minn., 1994.

BRIEF SUMMARY OF THE INVENTION

A pacemaker and tissue stimulation system has been described in previously noted co-pending applications. In the system described in those applications, an implanted (or external) controller-transmitter produces a pulsed ultrasound waveform, which is transmitted through body tissues to an implanted receiver-stimulator device. The transmitted ultrasonic waveform has an acoustic amplitude, pulse width, and pulse repetition period, which in a conventional pacemaker system would correspond to the pacing pulse electrical amplitude, pacing pulse width, and pacing cycle length, respectively. As in a conventional pacemaker system, all of the ultrasound parameters may be varied as required, either by physician control or automatically through real-time sensing of a variety of patient physiological conditions.

In the described system, the actual pacing pulse waveform applied to the tissue by the receiver-stimulator is the rectified form of the envelope of the received acoustic wave, which in turn is an attenuated copy of the transmitted acoustic wave. The invention described here provides a means to control the shape of the applied pacing pulse through control of the acoustic waveform transmitted by the controller-transmitter. The results of such control include the generation of more optimal pacing waveforms, enhanced energy efficiency of the acoustic pacing system, and reduced size of the implanted controller-transmitter.

In a first aspect of the present invention, a method for driving an implanted, acoustically powered receiver-stimulator comprises generating an acoustic transmission directed at the implanted receiver-stimulator. The receiver-stimulator will have at least one tissue-engaging electrode which engages tissue with a characteristic tissue-electrode impedance. The present invention relies on selecting acoustic transmission properties which compensate for the tissue-electrode impedance. Typically, the transmitted waveform will have a decreasing amplitude selected to compensate for the tissue-electrode impedance, more typically an exponentially decreasing amplitude. Usually, the final amplitude of the waveform will be from 40% to 60% of the initial amplitude. However, the transmission waveform may be of any shape selected to optimize the stimulation efficiency, after-potential reduction, or other parameter or combination of parameters.

Generating the acoustic transmission usually comprises supplying voltage to an acoustic transmitter amplifier and controlling the supplied voltage to produce an electrical waveform having a pre-selected envelope, which is then applied to an acoustic transducer. The acoustic transducer, in turn, generates an acoustic transmission with a waveform having the same envelope as the electrical waveform. The supplied voltage is typically controlled by a power supply, typically a DC-DC converter and an energy storage capacitor; however it may be generated and controlled by any number of known means.

In a second aspect of the present invention, a method for delivering an electrical stimulation pulse to tissue comprises implanting a controller-transmitter and a receiver-stimulator in a patient. The controller-transmitter produces an acoustic transmission having a desired envelope and is powered by circuitry including an energy storage capacitor. The receiver-stimulator comprises circuitry including an envelope detector to produce an electrical stimulation pulse having a voltage proportional to the amplitude of the acoustic transmission from the controller-transmitter. The electrical stimulation pulse is delivered from the receiver-stimulator to tissue by electrodes having a tissue-electrode impedance. The capacitance of the energy storage capacitor in the controller-transmitter circuitry is selected to produce an acoustic transmission with a constant envelope amplitude, or more preferably a decreasing envelope amplitude, and most preferably an exponentially decreasing amplitude. The decreasing envelope amplitude compensates for the tissue-electrode impedance of the electrodes.

Preferably, the stimulation pulse which is delivered to tissue is directed at cardiac tissue to effect cardiac pacing. More preferably, the acoustic transmission waveform will have a specific envelope selected to compensate for the tissue-electrode impedance which results from a stimulation pulse having a rectangular shape.

In a third aspect of the present invention, a system for delivering an electrical stimulation pulse to tissue comprises a controller-transmitter and a receiver-stimulator. The nature of the controller-transmitter and receiver-stimulator have been described above with respect to the method for delivering an electrical stimulation pulse to tissue.

In a fourth aspect of the present invention, an acoustic transmitter for driving an implanted acoustically powered receiver-stimulator comprises acoustic transmission generating circuitry and electrical power supply circuitry. The electrical power supply circuitry includes a battery and an energy storage capacitor connected to power the acoustic transmission generating circuitry. The acoustic transmission generating circuitry produces an acoustic transmission having a decreasing envelope amplitude so that the energy that must be supplied to the acoustic transmission generating circuitry by the energy storage capacitor is less than the energy required to produce an acoustic transmission having a constant envelope amplitude. Thus, energy required from the battery can be reduced and battery life of the implanted controller-transmitter increased significantly, or conversely, for a given battery lifetime requirement a smaller capacity battery may be employed.

In a fifth aspect of the present invention, an acoustic transmitter for driving an implanted acoustically powered receiver-stimulator comprises acoustic transmission generating circuitry and electrical power supply circuitry. The power supply circuitry includes both a battery and an energy storage capacitor, which are connected to power the acoustic transmission generating circuitry. The capacitance of the energy storage capacitor will be selected to produce an acoustic transmission having a decreasing envelope amplitude, where the capacitance is less than that which would be required to produce an acoustic transmission with a constant envelope amplitude. In this way, the physical size of the energy storage capacitor is significantly reduced.

DETAILED DESCRIPTION OF THE INVENTION

Figure 1:
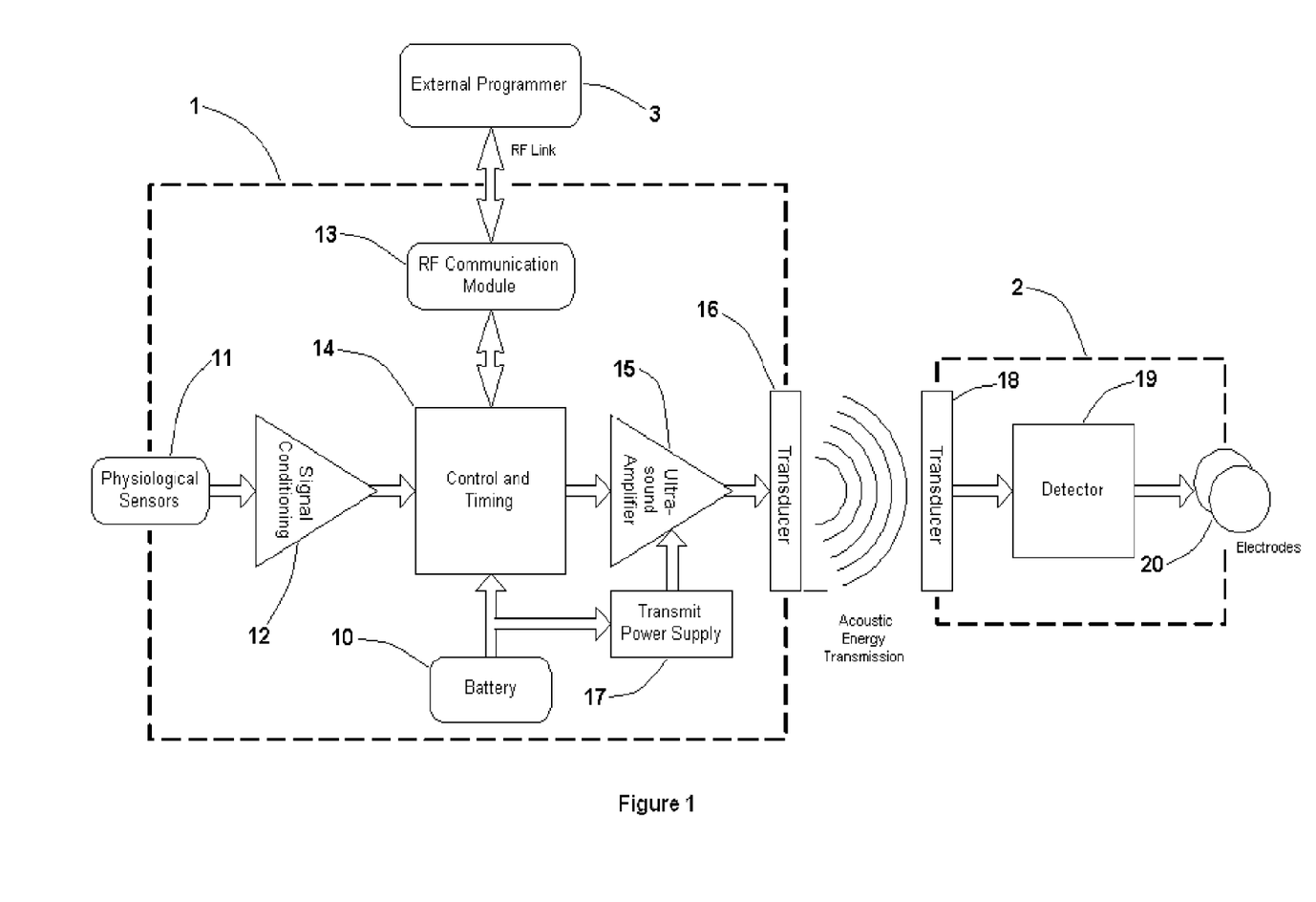
FIG. 1 is a block diagram of an acoustic cardiac pacemaker system of the type which can be modified to consume less energy in accordance with the principles of the present invention.

An acoustic cardiac pacemaker system as previously described in co-pending applications is shown in the block diagram of FIG. 1. The controller-transmitter device 1 is comprised of: a battery 10 which is optionally a rechargeable battery; multiple electrodes and possibly other sensors including motion sensors 11, which may be in direct contact with tissue to detect the patient's electrocardiogram, pacing signals from other conventional pacemakers, and other physiological parameters possibly including patient activity; these being connected to signal processing circuitry 12; a communications module 13 whose function is to provide a data path, for example by RF communication, to and from an external programmer unit 3 to allow the physician to set device parameters and to acquire diagnostic information about the patient and/or the device; a control and timing module 14 which stores such setup parameter and diagnostic information and uses this information in conjunction with the acquired physiological data to generate the required control signals for the ultrasound transmit amplifier 15 which in turn applies electrical energy to the transmitting ultrasound transducer 16 which ultimately produces the desired acoustic beam. A transmit power supply 17, typically a DC-DC converter, provides a voltage typically higher than the voltage of battery 10, which is used by the ultrasound transmit amplifier 15.

Referring also to FIG. 1, a receiver-stimulator device 2, implanted in the path of the acoustic beam at the location where electrical stimulation is desired, contains a receiving ultrasound transducer 18 which intercepts a portion of the transmitted acoustic energy and converts it into an alternating electrical signal representing the alternating nature of the applied ultrasound pressure wave. This electrical signal is applied to an electrical circuit 19, which may be one of a type commonly known as an envelope detector, and which may have one of many known circuit configurations, producing a voltage pulse with amplitude proportional to the amplitude of the transmitted acoustic waveform and with a pulse length generally equal to the length of the transmitted acoustic waveform. The circuit 19 may also be of different configurations and function, for example to provide a fixed delay between the reception of the acoustic energy and the output of the pacing pulse, or to provide output signals having characteristics other than a single pulse. This signal is applied then to electrodes 20 which may be incorporated onto the outer surface of the device, and thus in direct contact with the tissue which is to be stimulated.

Figure 2:
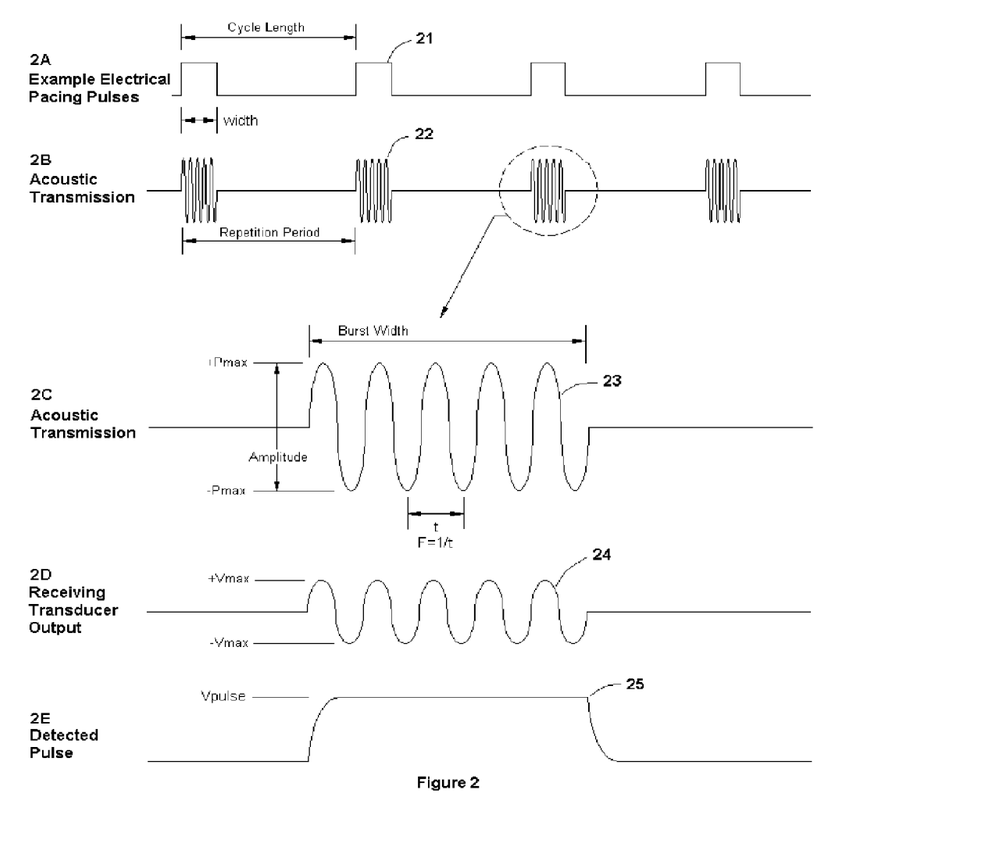
FIGS. 2A-2E are simplified representations of the acoustic and electrical signals of the acoustic pacemaker system shown in FIG. 1.

FIG. 2 is a simplified representation of the acoustic and electrical signals of an acoustic pacemaker system shown in FIG. 1 and previously described in co-pending applications. FIG. 2A depicts a train of pacing pulses 21 such as those that may be generated by any conventional electrical pacemaker, wherein each pulse has a desired width and is repeated at a desired cycle length. Similarly, the controller-transmitter device 1 produces acoustic transmissions 22, as shown in FIG. 2B, having the desired pacing pulse width and repeated at the desired pacing cycle length, which are emitted from the ultrasound transducer 16. FIG. 2C shows an enlargement 23 of a single acoustic transmission from the pulse train depicted in FIG. 2B. This transmitted burst has a desired width, a desired oscillation frequency $F=1/t$, and also a desired acoustic pressure amplitude indicated by the maximum positive pressure $+P_{max}$ and maximum negative pressure $-P_{max}$. The acoustic pressure wave, when striking the receiving transducer 18 of the receiver-stimulator device 2 generates an electrical signal 24, as shown in FIG. 2D, having frequency and burst width matching that of the transmitted acoustic waveform 23 and amplitude indicated by the maximum positive voltage $+V_{max}$ and maximum negative voltage $-V_{max}$ which are proportional to the transmitted acoustic pressure $(\sim+-P_{max})$. FIG. 2E shows this electrical waveform 24 after it has been rectified and filtered by the circuit 21 producing a desired pulse 25 with length equal to the burst length of the transmitted waveform 23 and amplitude $(V_{pulse})$ proportional to the amplitude of the electrical signal 24. It can be seen in this example that it is possible to vary the pacing rate by varying the repetition period between ultrasound bursts, to vary the duration of any one pacing pulse by varying the duration of the ultrasound burst, and to vary the amplitude of the pacing pulse by varying the amplitude of the ultrasound waveform.

The waveform shown in FIG. 2E would be generated in a practical design of such an acoustic pacemaker system, if the electrical load applied to the electrodes 20 were a linear (e.g., resistive) load. However, in practice a more complex impedance is presented to the stimulating electrodes due to polarization at the electrode-tissue interface. This effect is well-known and the resulting impedance seen by a typical pacemaker electrode has been modeled electrically as the circuit shown in FIG. 3 (Soykan).

Figure 3:
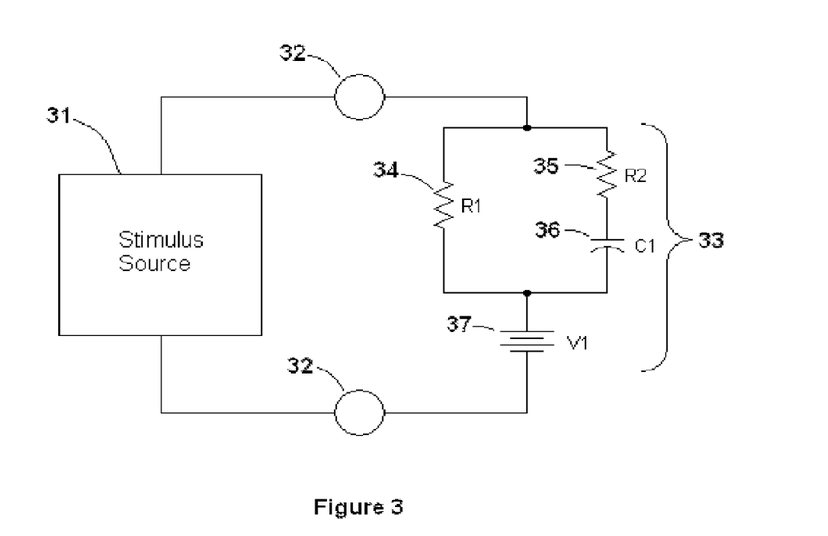
FIG. 3 is a tissue-electrode impedance model characteristic of applying a stimulation pulse to tissue in accordance with the principles of the present invention.

In FIG. 3, a stimulus source 31 produces a stimulation pulse, which is applied to the tissue through electrodes 32. Source 31 can be either a conventional pacemaker-lead system or an acoustic receiver-stimulator 2. The tissue interface impedance model is represented by the circuit 33, comprised of resistor 34 in parallel with resistor 35 and capacitor 36. A voltage source 37 represents the cellular transmembrane potential, which is approximately 80 mV. The actual values of R1, R2, and C1 are dependent on many factors including electrode material and size, stimulation circuit output impedance, lead wire (if used) impedance, and age of the electrode-tissue interface. Values determined from acute in-vivo studies with a prototype implantable receiver-stimulator are:

R1=6150 Ω
R2=400 Ω
C1=1.2 µF
V1=negligible

Figure 4:
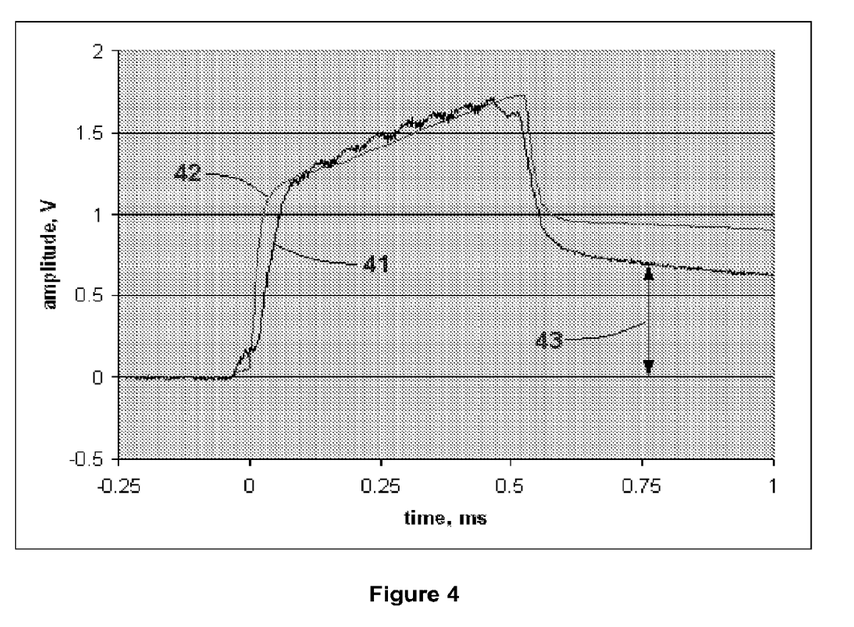
FIG. 4 is a graph showing pacing stimulus from an implantable receiver-stimulator device under both in vivo and in vitro conditions.

FIG. 4 shows a recorded pacing stimulus 41 from an in-vivo use of a prototype implantable receiver-stimulator device. Superimposed on this graph is a waveform 42 from the same prototype device obtained in-vitro, terminated with a circuit as shown in FIG. 3 fabricated with the above component values. Very good agreement between in-vivo and in-vitro results is demonstrated.

However, it is important to note, in the context of this invention, that due to the electrode-tissue impedance, the pacing stimulus 41 generated by the acoustic receiver-stimulator no longer approximates the rectangular shape of the envelope of the transmitted acoustic signal, as shown in the ideal case of FIG. 2E. Additionally, it is rather opposite in nature to a more desirable pulse shape, which as described earlier, is generated by the capacitively-coupled output of most conventional electrical pacemaker systems. Also, it contains a significant after-potential component 43 due to the electrode-tissue impedance.

The main objectives of this invention are 1) to produce in an acoustic pacemaker system a more desirable pacing pulse shape; 2) enhance the energy efficiency of such a system; and 3) to improve the packaging characteristics (reduce the overall volume) of the controller-transmitter. It will be shown that this invention will accomplish these goals; however, first, an understanding of an exemplary ultrasound transmitter amplifier will be useful.

Though a complete electrical model is more complex, a piezoelectric ultrasound transducer, such as those that may be used in an acoustic pacemaker system, can be simply characterized as presenting a highly-capacitive, relatively low impedance load to the transmitter amplifier. In such an application, as well as many others, it may be necessary to apply an oscillating waveform of hundreds of Volts peak-to-peak (Vp-p) to the piezoelectric transducer to generate the desired acoustic output. Such a high peak-to-peak voltage across a low impedance load produces high peak currents. One experimental transducer developed for a non-implantable acoustic pacemaker system utilized a 0.89 inch diameter piezoelectric transducer operating at 330 kHz, typically requiring 500 Vp-p and 0.5 Amperes peak (Ipk). Many other transducer sizes and frequencies may be utilized and therefore the transducer impedance and required drive characteristics may differ, as could be expected. However, the requirement to provide relatively high drive voltage and current remains universal.

Figure 5:
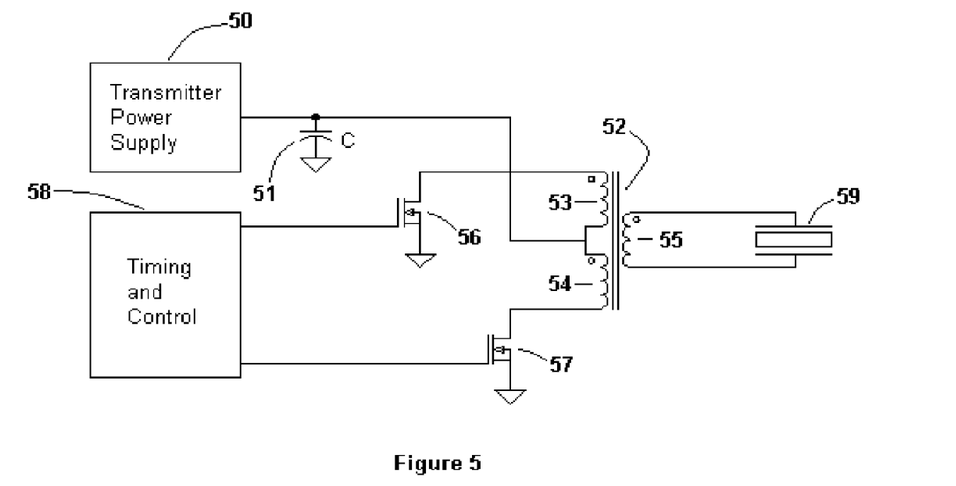
FIG. 5 is an electrical circuit model which is used to demonstrate the effect of varying the capacitance of the capacitor in delivering an electrical stimulation pulse.

Many amplifier designs are capable of supplying the required drive voltage and current to the described ultrasound transducers. As an illustrative example, one commonly used topology is a "Class D" transformer-coupled pulse amplifier, a simplified schematic diagram of which is shown in FIG. 5. Such an amplifier is well-suited for providing high-voltage, high-current drive signals into a low impedance load, typically operating in a burst mode at a low duty cycle (percentage of on-time to off-time). For an acoustic pacemaker, the duty cycle will typically be less than 0.5% (2 ms pacing pulse width at a pacing rate of 150 beats/minute), and preferably 0.1% (0.5 ms pacing pulse at 80 beats/minute) or less.

In the amplifier of FIG. 5, a power supply 50, which is typically a DC-to-DC converter and which may have a variable output voltage, provides a DC voltage to the center tap of a transformer 52 having dual, identical primary windings 53 and 54, and a secondary winding 55 having different number of turns than the primary windings. The ratio of turns between the primary and secondary is typically expressed as 1:N. Typically, the secondary winding will have considerably more turns than each primary winding. As one example the turns ratio of a transformer may be 1:4, wherein the primary windings may each have 10 turns and the secondary winding may have 40 turns. The secondary winding is connected to transducer 59. The connections of the primary windings opposite the center tap are connected to electronic switching devices 56 and 57, which are typically MOSFET devices, though other devices such as bipolar transistors or IGBTs could be used. In this example, the gate connections of the MOSFET devices are driven by the timing and control electronics 58 (also 14 in FIG. 1). Though neither MOSFET device is switched on the majority of the time, during a pacing pulse the two devices are alternately enabled and disabled, 180 degrees out of phase relative to one another, at the frequency of ultrasound transmission. It can be seen that when the first MOSFET device 56 is switched on current will flow from through primary 53 to ground, inducing a positive voltage equal to NV across the transducer. MOSFET 56 is then switched off by the circuitry 58 and MOSFET 57 is switched on. Current now flows from the center tap through primary 54 to ground, inducing a voltage equal to −(NV) across the transducer. Thus, the peak-to-peak voltage produced across the transducer is 2 NV, resulting in an acoustic output waveform as shown in FIG. 2B. Using exemplary component values and transducer drive voltage, the voltage and current requirements of the primary side may be found:

Example Parameters:

| Transducer impedance | 50 Ω |
| Transducer drive voltage (Vp-p) | 200 V (70.7 Vrms) |
| Peak current to transducer (Ipk) | 2.0 A (1.414 Arms) |
| Transformer turns ratio 1:N | 1:4 |
| Transformer impedance ratio $N^2$ | 16 |

Resulting Primary Voltage and Currents:

| Supply voltage to transformer primary | 25 V |
| Peak supply current to transformer primary | 4.0 A |
| Average current requirement with 0.1% duty cycle | 4 mA |

Neglecting any quiescent supply currents required by the amplifier circuitry, there is a large (1000:1) difference between peak and average amplifier current. In many applications, and in particular in a design intended for implanted, battery-powered operation, it is not practical to include a power supply capable of supplying a sustained high current output. Instead, a capacitor 51 stores energy which is used during the ultrasound transmit. This capacitor is recharged between transmit bursts to the required voltage by a power supply having a current capability closer to the average current rather than the peak current.

The value of capacitor 51 required to maintain an acceptably constant transmit voltage can be calculated once the voltage and current requirements of the transmit burst are known, and an assumption of the maximum supply voltage deviation, or droop, from the nominal value is made. The required capacitance can be obtained, once the energy requirement of the transmission burst is known, from the equation describing the energy stored in a capacitor, which is $E=1/2CV^2$ (Joules).

The transmit burst energy is the product of the supply voltage and the supply current, multiplied by the time duration of the burst. Assuming the load is constant, both V(t) and I(t) in this case vary during the transmission burst due to the exponential discharge of the storage capacitor, even if the capacitor is sufficient to keep the transmit voltage relatively constant. $V(t)=V_{start}e^{-t/k}$ and $I(t)=I_{start}e^{-t/k}$. If we allow a modest 5% droop in the power supply voltage during the transmission burst, and specify that the desired pacing pulse width is 0.5 ms, then k=9.75 ms, the time constant resulting in a 5% exponential decay in 0.5 ms. To determine the energy, the product of V(t) and I(t) is integrated over the 0.5 ms transmit period:

$$E \text{ (Joules)} = \int_0^t V_{start} e^{-t/k} I_{start} e^{-t/k} dt$$

$$= V_{start} I_{start} \int_0^t e^{-2t/k} dt$$

$$= V_{start} I_{start} \left[ -\frac{k}{2} e^{-2t/k} \right]_0^T$$

$$= \frac{k}{2} V_{start} I_{start} [1 - e^{-2T/k}]$$

Inserting the initial voltage and current requirements from the above example:

$$E = \frac{9.75 \times 10^{-3}}{2} (25)(4) \left[1 - e^{(-2)(5 \times 10^{-4})/9.75 \times 10^{-3}}\right] = 47.52 \text{ mJ}$$

Now, rearranging $E=1/2CV\cdot\text{sup}\cdot 2$ and substituting the calculated energy, and using the starting and ending transmit supply voltages:

$$C_{required} = 2E/(V_{start}^2 - V_{end}^2) = 2(47.52 \times 10^{-3})/(25^2 - 23.75^2) = 1560 \text{ μF}$$

Figure 6:
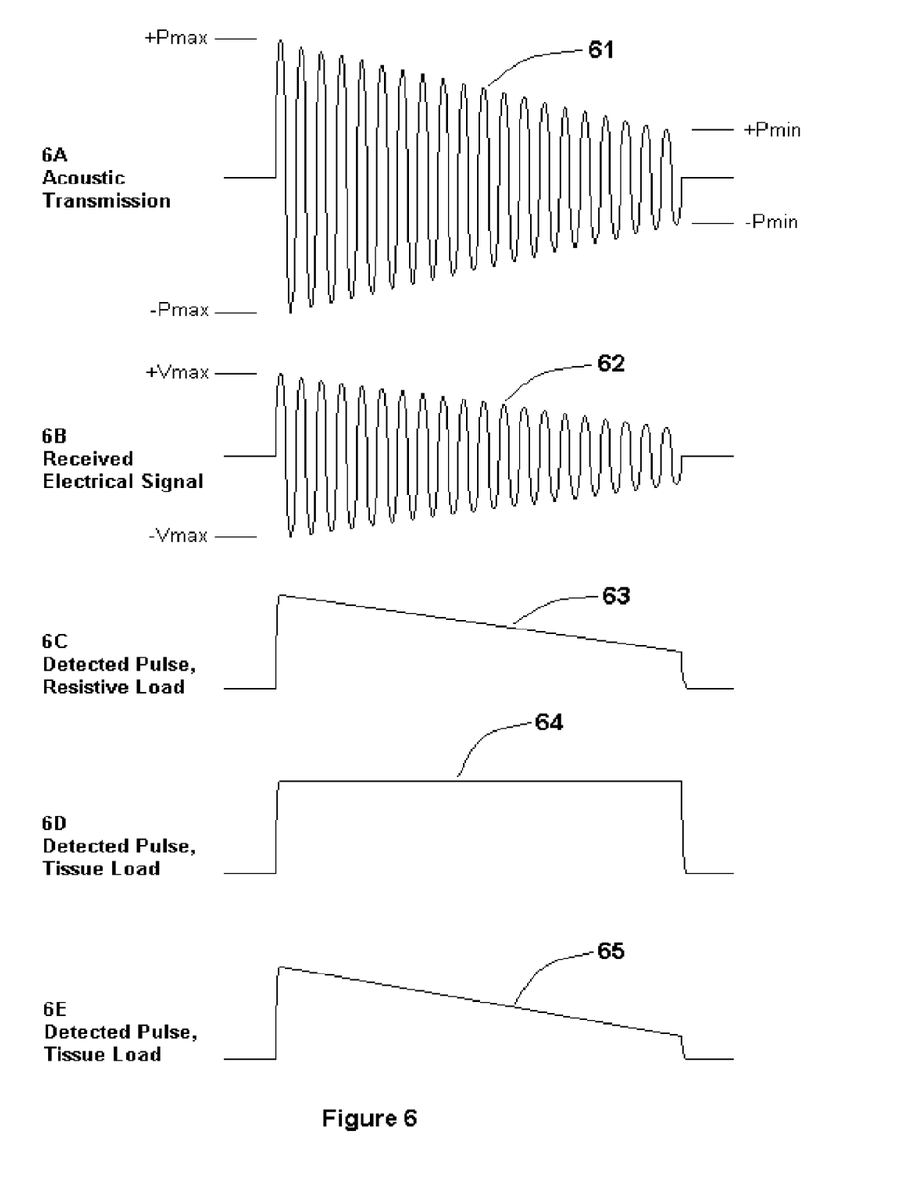
FIG. 6A-6E are simplified representations of the acoustic and electrical signals having modified envelope geometries produced by the controller-transmitter and receiver-stimulator devices in accordance with the principles of the present invention.

Considering the waveforms of FIGS. 2C through 2E, and the discussion of the actual impedance seen by the stimulator modeled in FIG. 3 and its effect on the in-vivo shape of the stimulation pulse, FIG. 6 presents a method to alter the shape of the stimulation pulse generated by the acoustic receiver-stimulator to compensate for the impedance effect. FIG. 6A shows a modified acoustic transmission waveform 61 which initially reaches the same peak positive and negative acoustic pressure levels ±P$_{max}$ as in transmission waveform 23 of FIG. 2C. However, the amplitude of waveform 61 decays from this initial value to the lower values ±P$_{min}$. This decay may be linear, exponential, or any other shape.

In FIGS. 6B and 6C, the electrical signal 62 generated by the acoustic receiver, and the resulting detected waveform 63 (as if terminated into a resistive load), are shown. FIG. 6D, however, shows the waveform 64 that results if the same stimulus waveform 63 is applied to the tissue-electrode equivalent circuit of FIG. 3. The result is a more rectangular pulse. This concept is easily extended to produce a more desirable waveform such as 65 shown in FIG. 6E, similar to the output waveform of most current electrical pacemakers, by providing still further decay in the transmitted acoustic signal to over-compensate for the effect of the load impedance.

Referring back to FIG. 5 and in particular the energy storage capacitor 51, it can be seen that a simple way to achieve at least one desired transmit shape would be to reduce the value of capacitor 51 to allow significant decay of the transmitter supply voltage during the acoustic transmission time. Repeating the above calculations but allowing a 50% drop in transmitter supply voltage during the transmit burst, a new value for the required capacitor is obtained as above, by first determining the energy expended during the transmit burst, and using that value to determine the necessary capacitance.

As before, to determine the energy, the product of V(t) and I(t) is integrated over the 0.5 ms transmit period, this time using a time constant k=0.721 ms to allow a 50% droop in the transmit supply voltage during the transmit burst.

$$E \text{ (Joules)} = \frac{.721 \times 10^{-3}}{2} (25)(4) \left[1 - e^{(-2)(5 \times 10^{-4})/.721 \times 10^{-3}}\right] = 27.04 \text{ mJ}$$

Then as before, $$C_{required} = 2E/(V_{start}^2 - V_{end}^2) = 2(27.04 \times 10^{-3})/(25^2 - 12.5^2) = 115.4 \text{ μF}$$

These values can be compared with the corresponding values of a constant-amplitude acoustic transmission, which requires in this example 47.5 mJ and a capacitor of 1560 μF.

Figure 7A:
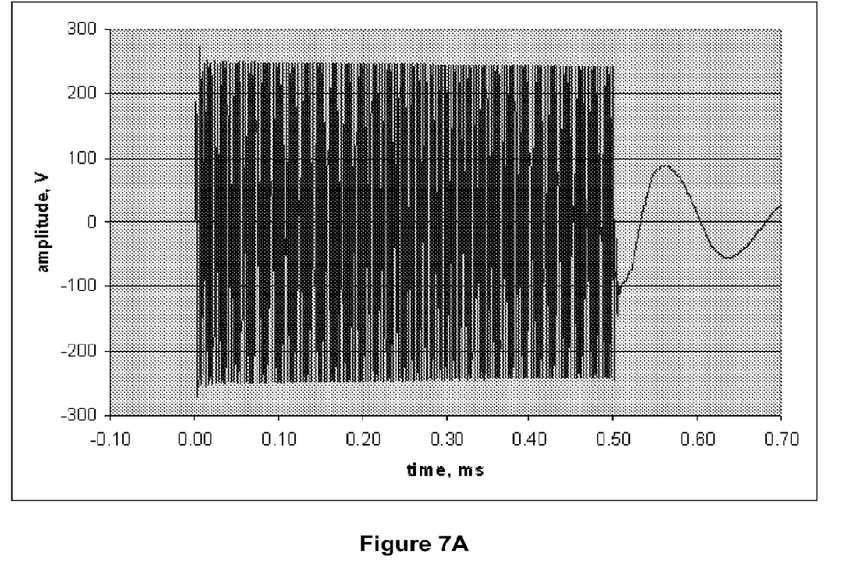
FIGS. 7A and 7B are oscilloscope recordings of representative electrical waveforms provided to the acoustic transmitter of the controller-transmitter of the present invention.
Figure 7B:
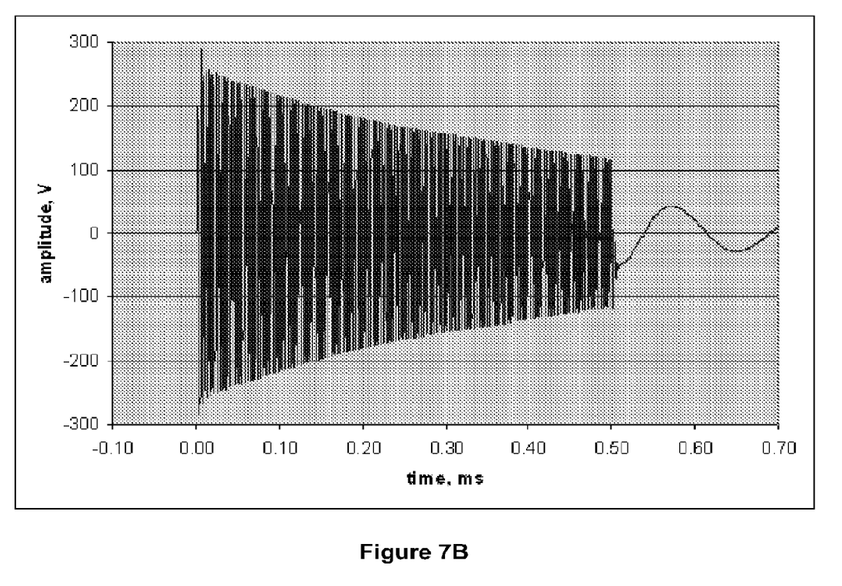

FIGS. 7A and 7B show representative electrical drive waveforms supplied by the transmitter amplifier to the acoustic transducer. FIG. 7A is an oscilloscope recording of the electrical output from a prototype transmitter amplifier of a 0.5 ms transmit burst at 330 kHz. The amplifier that was used to record the trace in FIG. 7A has a storage capacitor as 51 in FIG. 5 sized to minimize amplitude droop during the transmit burst. In this waveform, the initial transmitter output amplitude is 510 Vp-p and the amplitude at the end of the transmit burst is 485 Vp-p, corresponding to a 4.9% drop during the transmit burst. FIG. 7B is an oscilloscope recording of a similar transmit burst. However, in this case the storage capacitor 51 has been reduced to result in the more desirable transmitter output. In this recording, the initial transmitter output amplitude is 506 Vp-p and the final amplitude is 234 Vp-p, corresponding to a 53.8% droop during the transmit burst. Comparing FIG. 7B to FIG. 7A, it is clearly demonstrated that less energy is used in the transmitted waveform FIG. 7B.

Figure 8:
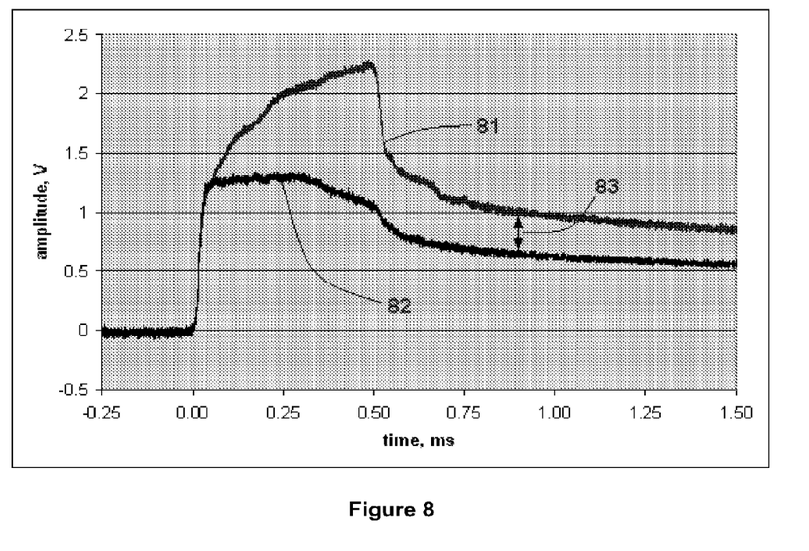
FIG. 8 is an oscilloscope recording of the output of a prototype acoustic receiver-stimulator device in an acoustic pacemaker system constructed in accordance with the principles of the present invention.

FIG. 8 shows the result of applying this concept to an in vivo use of a prototype acoustic receiver-stimulator device. Waveform 81 shows an oscilloscope recording of a pacing stimulus generated without application of this invention, with a transmit burst as in FIG. 7A. Waveform 82 shows a recorded pacing stimulus with the application this invention, with a transmit burst as in FIG. 7B, producing a waveform shape similar to the output waveform of current electrical pacemakers. This more desirable pacing stimuli waveform also exhibits a desirable reduction in after-potential 83 at the electrodes.

In summary, it has been shown that modifying the shape of an acoustic transmission waveform in an acoustic pacemaker can compensate for the electrode-tissue impedance and improve energy efficiency. A simple method to achieve such a modification includes reducing the capacitance in the transmitter power supply circuitry. The reduction in capacitance results in not only a more desirable waveform shape, but also contributes a significant reduction in the energy expended during each transmit burst, 28% in this example, but may be greater or lesser depending on the desired transmit waveform and transducer drive requirements. Energy reduction in each transmit burst ultimately affects the longevity of the implanted device given a certain battery capacity. Conversely, it would allow the use of a physically smaller battery for a given device lifetime, resulting in a smaller overall implanted controller-transmitter package. Such a change also directly affects the physical size of the implanted controller-transmitter package by reducing the physical size of the storage capacitor. The volume of a capacitor with a given working voltage is roughly proportional to its capacitance, thus a reduction of better than ten-fold in capacitor volume could be expected from the given example.

What is claimed is:

1. A method for driving an implanted acoustically powered receiver-stimulator having at least one tissue-engaging electrode with a tissue-electrode impedance, said method comprising:
   directing an acoustic transmission towards the implanted receiver-stimulator, said transmission having an envelope selected to compensate for the tissue-electrode impedance; and
   wherein directing the acoustic transmission is generated by supplying voltage to an acoustic transmitter amplifier and controlling the supplied voltage to produce an acoustic transmission having a pre-selected envelope, and wherein the supplied voltage is controlled by selecting the capacitance of an energy storage capacitor in a transmitter voltage power supply circuit.

2. A method as in claim 1, wherein said transmission has a decreasing amplitude.

3. A method as in claim 2, wherein said transmission has an exponentially decreasing amplitude.

4. A method as in claim 2, wherein the amplitude has an initial and final value and the final amplitude of the transmission is from 40% to 60% of the initial amplitude.

5. A method as in claim 1, wherein said envelope is configured with a pre-selected shape.

6. A method as in claim 1, wherein the acoustic transmission is generated by an implanted controller-transmitter.

7. A method as in claim 1, wherein the acoustic transmission is generated by an external controller-transmitter.

8. A method for driving an implanted acoustically powered receiver-stimulator having at least one tissue-engaging electrode with a tissue-electrode impedance, said method comprising:
   directing an acoustic transmission towards the implanted receiver-stimulator, said transmission having an envelope selected to compensate for the tissue-electrode impedance; and
   wherein said transmission has an exponentially decreasing amplitude, wherein the amplitude has an initial and final value and wherein the final amplitude of the transmission is from 40% to 60% of the initial amplitude.

9. A method as in claim 1, wherein said envelope is configured with a pre-selected shape.

10. A method as in any of claims 8, wherein directing the acoustic transmission is generated by supplying voltage to an acoustic transmitter amplifier and controlling the supplied voltage to produce an acoustic transmission having a pre-selected envelope.

11. A method as in claim 10, wherein the supplied voltage is controlled by selecting the capacitance of an energy storage capacitor in a transmitter voltage power supply circuit.

12. A method as in claim 8, wherein the acoustic transmission is generated by an implanted controller-transmitter.

13. A method as in claim 8, wherein the acoustic transmission is generated by an external controller-transmitter.

* * * * *